United States Patent
Kassab et al.

(10) Patent No.: US 11,262,299 B2
(45) Date of Patent: Mar. 1, 2022

(54) METHOD AND APPARATUS FOR NON-INVASIVE CONDITION DETECTION USING AN ALL FIBER PORTABLE TERAHERTZ IMAGING SYSTEM

(71) Applicants: Ghassan S. Kassab, La Jolla, CA (US); Ali Dabiri, San Diego, CA (US)

(72) Inventors: Ghassan S. Kassab, La Jolla, CA (US); Ali Dabiri, San Diego, CA (US)

(73) Assignee: 3DT Holdings, LLC, San Diego, CA (US)

(*) Notice: Subject to any disclaimer, the term of this patent is extended or adjusted under 35 U.S.C. 154(b) by 0 days.

(21) Appl. No.: 15/630,643

(22) Filed: Jun. 22, 2017

(65) Prior Publication Data

US 2017/0370834 A1 Dec. 28, 2017

Related U.S. Application Data

(60) Provisional application No. 62/409,694, filed on Oct. 18, 2016, provisional application No. 62/353,225, filed on Jun. 22, 2016.

(51) Int. Cl.
*G01J 5/02* (2006.01)
*G01N 21/3586* (2014.01)
(Continued)

(52) U.S. Cl.
CPC ....... *G01N 21/3586* (2013.01); *A61B 5/0042* (2013.01); *A61B 5/02042* (2013.01);
(Continued)

(58) Field of Classification Search
CPC .......... A61B 5/0066; A61B 2562/0238; A61B 2018/207; A61B 5/0042; A61B 5/0064; A61B 5/02042; A61B 5/4088; A61B 5/0075; A61B 5/0265; A61B 5/6833; A61B 5/7203; A61B 2560/0223; A61B 5/0507; G01N 21/3581; G01N 21/3586; G01N 2201/06113; G01N 2800/2821;
(Continued)

(56) References Cited

U.S. PATENT DOCUMENTS

| 5,905,707 A | * | 5/1999 | Ju | G11B 7/1353 369/112.08 |
| 6,747,736 B2 | * | 6/2004 | Takahashi | G01N 21/3581 356/319 |

(Continued)

*Primary Examiner* — Kiho Kim
(74) *Attorney, Agent, or Firm* — William F. Ward

(57) ABSTRACT

Method and apparatus for non-invasive condition detection using an all fiber portable terahertz imaging system. An imaging system of the present disclosure may comprise a control module comprising a femtosecond pulsed laser configured to generate an output light beam, a dispersion compensation unit configured to receive the output light beam and transmit a laser light beam generated based upon the output light beam, a beam splitter configured to receive the laser light beam and divide the laser light beam into a pump light beam and a reference light beam; and a rapid scanning optical delay line configured to receive the pump light beam and transmit an exit light beam generated based upon the pump light beam, a patch probe comprising a transmitter module, an optics lens, and a detector module.

12 Claims, 5 Drawing Sheets

(51) Int. Cl.
*G01N 21/39* (2006.01)
*G01J 3/42* (2006.01)
*A61B 5/0507* (2021.01)
*G01J 3/10* (2006.01)
*G01V 3/12* (2006.01)
*G01N 21/3563* (2014.01)
*A61B 5/00* (2006.01)
*A61B 5/02* (2006.01)
*G01N 21/3581* (2014.01)
*A61B 5/0265* (2006.01)

(52) U.S. Cl.
CPC .......... *A61B 5/0507* (2013.01); *A61B 5/4088* (2013.01); *G01J 3/10* (2013.01); *G01J 3/42* (2013.01); *G01N 21/3563* (2013.01); *G01N 21/3581* (2013.01); *G01N 21/39* (2013.01); *G01V 3/12* (2013.01); *A61B 5/0075* (2013.01); *A61B 5/0265* (2013.01); *A61B 5/6833* (2013.01); *A61B 5/7203* (2013.01); *A61B 2560/0223* (2013.01); *G01N 2201/0221* (2013.01)

(58) Field of Classification Search
CPC ............. G01N 33/483; G01N 21/1702; G01N 21/3563; G01N 21/39; G01N 21/636; G01N 2201/0221; G01J 3/42; G01J 3/10; G01V 3/12; A61L 35/0075; A61L 35/0265; A61L 35/7203
USPC ...................................................... 250/341.1
See application file for complete search history.

(56) References Cited

U.S. PATENT DOCUMENTS

| | | | | |
|---|---|---|---|---|
| 6,839,172 B1* | 1/2005 | Motamedi | .......... | G02B 26/0866 359/17 |
| 7,828,438 B1* | 11/2010 | Motamedi | .............. | A61B 3/102 351/221 |
| 2002/0023903 A1* | 2/2002 | Ann Ngoi | .......... | B23K 26/0624 219/121.68 |
| 2002/0067480 A1* | 6/2002 | Takahashi | ............... | G01N 21/49 356/317 |
| 2004/0100637 A1* | 5/2004 | Teich | ................. | G01B 9/02007 356/497 |
| 2004/0249261 A1* | 12/2004 | Torchia | .................. | A61B 18/22 600/411 |
| 2005/0094511 A1* | 5/2005 | Nakao | .................. | G11B 7/1381 369/44.37 |
| 2005/0163426 A1* | 7/2005 | Fermann | ............... | H01S 3/1115 385/37 |
| 2005/0254049 A1* | 11/2005 | Zhao | .................. | G01N 21/8422 356/369 |
| 2006/0170930 A1* | 8/2006 | Li | ....................... | G01B 9/02091 356/479 |
| 2007/0019276 A1* | 1/2007 | Zeng | ......................... | G02F 1/33 359/285 |
| 2007/0263226 A1* | 11/2007 | Kurtz | ................. | G01N 21/6458 356/492 |
| 2008/0039718 A1* | 2/2008 | Drinan | ..................... | A61B 5/05 600/427 |
| 2008/0140341 A1* | 6/2008 | Ralston | ............... | G01B 9/02091 702/155 |
| 2009/0221920 A1* | 9/2009 | Boppart | ................ | A61B 5/6853 600/476 |
| 2009/0225311 A1* | 9/2009 | Umetsu | ...................... | G01J 3/10 356/317 |
| 2009/0225313 A1* | 9/2009 | Umetsu | ................. | G01J 3/0278 356/326 |
| 2010/0121199 A1* | 5/2010 | Dabiri | .................. | A61B 5/0062 600/476 |
| 2010/0214562 A1* | 8/2010 | Mahadevan-Jansen | ..................... | A61B 5/0059 356/301 |
| 2010/0232279 A1* | 9/2010 | Stevenson | .......... | G11B 7/00455 369/100 |
| 2010/0246343 A1* | 9/2010 | Yamasaki | ............ | G11B 7/0956 369/44.32 |
| 2011/0130652 A1* | 6/2011 | Boppart | .................. | A61B 3/102 600/425 |
| 2011/0280262 A1* | 11/2011 | Fermann | ............... | H01S 3/1112 372/3 |
| 2012/0068090 A1* | 3/2012 | Park | ....................... | H01S 5/4031 250/493.1 |
| 2012/0143065 A1* | 6/2012 | Sanchez | ............. | A61B 1/00045 600/478 |
| 2012/0250133 A1* | 10/2012 | Stewart | ................ | G02B 26/001 359/238 |
| 2013/0314717 A1* | 11/2013 | Yi | .......................... | G01N 21/45 356/479 |
| 2014/0028997 A1* | 1/2014 | Cable | ................. | G01B 9/02067 356/51 |
| 2014/0142430 A1* | 5/2014 | Slayton | ................ | A61B 8/4483 600/439 |
| 2014/0148834 A1* | 5/2014 | Barthe | ................ | G01S 15/8909 606/169 |
| 2014/0152997 A1* | 6/2014 | Goldberg | ................ | H01S 5/141 356/479 |
| 2014/0180174 A1* | 6/2014 | Slayton | ................ | G01S 15/899 601/2 |
| 2014/0288542 A1* | 9/2014 | Torchia | .................. | A61B 18/22 606/12 |
| 2015/0103355 A1* | 4/2015 | Bower | .................... | A61B 3/102 356/479 |
| 2015/0141846 A1* | 5/2015 | Sanchez | ............. | A61B 1/00165 600/478 |
| 2016/0007879 A1* | 1/2016 | Gonzalez | ................ | A61B 5/6814 600/306 |
| 2016/0103307 A1* | 4/2016 | Frankel | ................ | G02B 21/0028 600/317 |
| 2016/0270656 A1* | 9/2016 | Samec | .................. | A61B 5/6803 |
| 2018/0156600 A1* | 6/2018 | Cable | ................. | H01S 5/0651 |

* cited by examiner

METHOD AND APPARATUS FOR NON-INVASIVE CONDITION DETECTION USING AN ALL FIBER PORTABLE TERAHERTZ IMAGING SYSTEM

PRIORITY

The present application is related to, and claims the priority benefit of, U.S. Provisional Patent Application Ser. No. 62/353,225, filed Jun. 22, 2016, and U.S. Provisional Patent Application Ser. No. 62/409,694, filed Oct. 18, 2016, the contents of which are expressly incorporated herein directly and by reference in their entirety.

FIELD OF THE DISCLOSURE

The present disclosure includes disclosure of methods and apparatuses related to non-invasive hemorrhage detection using an all fiber coupled portable terahertz imaging system (PTIS). The present disclosure also includes disclosure of methods and apparatuses related to non-invasive early detection of Alzheimer's through eye cornea/aqueous humor ("AH," the clear fluid filling the space in the front of the eyeball between the lens and the cornea) using an all fiber coupled portable terahertz imaging system (PTIS).

BACKGROUND

Internal bleeding remains the leading cause of preventable death in trauma and battlefield and early detection of hemorrhage can improve outcome. Historically, approximately 20% of the combat casualties are killed in action (KIA), defined as being killed before reaching a treatment facility. The major causes of death in this group are hemorrhage (50%) and neurological trauma (36%), whereas the rest are from devastating multiple injuries. Even when the injured survive long enough to be transported to a medical facility, hemorrhage still remains the leading cause of late death and complications (died of wounds (DOW)). The percentage of soldiers that are KIA has remained unchanged since the American Civil War (approximately 20%); however, the percentage of DOW has declined markedly over time. The DOW rates decreased from 8 to 2.5% between World War I and the Korean War. In the war in Iraq, the total number of casualties was low but the data from the early phase of the conflict showed an unchanged KIA rate. According to the information released by the Pentagon, by early September 2003 the total number of U.S. casualties in Iraq was 1,406 with 1,124 wounded (79.95%) and 282 dead (20.05%).

After a traumatic injury, hemorrhage is responsible for over 35% of pre-hospital deaths and over 40% of deaths within the first 24 hours second only to the rates of death due to severe central nervous system injury. A cascade of life-threatening medical problems can begin with severe hemorrhage, and many of these occur simultaneously. The severity of each problem is commonly associated with the extent of overall blood loss. Low blood pressure due to blood loss indicates immediate complications, including the incidence of multiple organ failure and life-threatening infections.

The hemorrhage detection is the most crucial step in order to control it. Visible blood is the most obvious sign, but sometimes the only way to know a hemorrhage has occurred inside the body is when it causes symptoms or an illness, such as shock or stroke. In the case of brain hemorrhage, depending on where the bleeding is occurring, symptoms can include headache, loss of function of one side of the body, vision changes, difficulty speaking, swallowing, reading, or writing, decreased alertness, vomiting, stiff neck, drowsiness, or coma. It is rather difficult to assess most of these symptoms since the soldier/patient is in the state of shock and cannot communicate.

Blood loss creates low blood volume and hence low blood pressure causing skin circulation vasoconstriction to allow more of the blood flow to vital organs (e.g. heart, brain, etc.). Skin vasoconstriction is the narrowing of the skin blood micro-vessels resulting from contraction of the pores of the skin. This process reduces the amount of blood and hence plasma (largely water) in the skin.

In view of the foregoing, there is a definite need for a simple non-invasive system that a) can detect an early sign of hemorrhage as well as the degree of severity, b) is low cost, c) is safe and simple to operate, and portable, and d) has high sensitivity and specificity.

Alzheimer's disease (AD) in a medical term is classified as a form of dementia, a group of conditions that gradually destroy brain cells. Alzheimer's generally appears in older persons, continuing steadily to disorder brain and gradually destroys a person's memory and ability to make judgments, communicate and carry out daily activities. Scientists now believe that the cause of AD is most likely due to the concentration of Beta-amyloid deposited in some part of the brain. As Alzheimer's progresses, patients may also experience changes in behavior during their personal lives, such as anger, agitation and sometimes even delusions or hallucinations.

There is not a cure and/or successful treatment for Alzheimer's. All the reported treatment methods do not show a light at the end of the tunnel. The results of the reported treatments are mostly either based on exercise, body treatment, or based on some herbal remedies and dietary supplements. One treatment reported by scientists at the University of South Florida promoting EGCG (epigallocatechin-3-gallate), which is found in green tea. The results indicated the notion that EGCG and other flavonoids, such as luteolin, are 'multipotent therapeutic agents' that not only reduce toxic levels of brain $A\beta$, but also hold the potential to protect neuronal mitochondrial function in AD.

In the past, several possible treatments for AD have been reported where all these are only effective on the early stages of Alzheimer's. For example, researchers from Rush University Medical Center in Chicago are working in gene transfer. This techniques and other similar methods are only promising if Alzheimer's is detected at its early stage of development.

If the patient is treated at the early stage of disease, the patient can have a relatively good life style even though he/she is not totally cured. Therefore, early detection and diagnosis of Alzheimer's is highly desirable. Many methods have been reported during the past decades in literature in addition to patents for Alzheimer's detection and diagnosis. Presently, there are no simple methods like blood or urine test that can detect Alzheimer's.

Following are several prior arts and methods that have been proposed for detection of Alzheimer's:

1. Testing the patient's memory by acorneag questions and studying the patient's family history to determine if Alzheimer's is present. This is not very reliable technique and it mostly is done by a family doctor as initial indication for Alzheimer's.

2. Brain scanning by such techniques as CT (computed tomography) and MRI (magnetic resonance imaging) could be used for AD diagnosis. The problem of these techniques is that they are only effective at the late stages of Alzheimer's which the damage is already done. PET (positron electron tomography) brain scans can detect early Alzheimer's by measuring the brain's use of glucose, an indication of energy use. Studies have found that Alzheimer's patients have reduced glucose metabolism in areas of the brain that are compromised, and PET scans have found signs of a slowdown in glucose metabolism in patient years before Alzheimer's was diagnosed. But these studies are not aimed at early detection. When you look at a large number of people you're following every year, you can see correlations over tip e but for any one case, you couldn't make the call. At the same time is an expensive procedure.

3. Researchers at New York University Medical Center have reported EEG (electroencephalogram) testing that measures electrical activity in the brain to pinpoint the early signs of Alzheimer's as warning signal. In this method, the measured brain activity of patient is compared to a standard activity of a patient with no Alzheimer's disease. This method still is at initial study stage and according to the scientists at Alzheimer's Association, there is concern that EGG study is too limited to be an effective predictor.

4. Researchers in the Netherlands reported that they can predict the early detection of Alzheimer's by measuring the size of two parts of the brain, the hippocampus, and amygdala. For those patients who have smaller sizes of these two parts against some standard have several time more likely to suffer from the Alzheimer's decease. The technique is still at study stage and mostly is looking for any type of dementia; they are not focusing on Alzheimer's. Another drawback of this technique is direct scanning of the brain which is likely harmful to patient.

5. Goldstein et al. described the accumulation of beta amyloid in supra-nuclear (cortical) cataracts of patients with Alzheimer disease (AD) in 2003 and they conclude from these studies that "the process (i.e. the accumulation of beta amyloid) that's going on in the brain is also going on in the eye. However, Michael et al. reported in 2014 that cataracts in eye lenses of AD donors do not contain substantial amounts of beta amyloid. This strongly suggests that cortical cataract, although it may be comorbid with AD in some cases, has no relation with the main pathological signature of AD i.e. accumulation of beta amyloid and that cortical cataract and AD are therefore not likely to be causally linked. This also means that cortical cataract cannot be considered as indicator and/or predictor of AD.

6. Michael et al. reported the accumulation of misfolded proteins that occurs in other parts of the eye, for instance, in the cornea, causing various disorders by deposition of amyloid-like proteins. Janciaskiene et al. in 2011 detected Alzheimer's peptides in the aqueous humor (the clear fluid filling the space in the front of the eyeball between the lens and the cornea).

7. Sianto et al. in U.S. Pat. No. 6,162,186 are claiming that AD Patients' autonomic nervous system is hypersensitive to the neural transmitter mediators (NTM), used as eye drops, with concentration so low that did not affect the pupil's diameter change and other pupil's characteristics applied on a person with no sign of being AD symptom. They use standard CCD camera to measure the change in a diameter and constriction of the pupil in the eye of an AD patient in a short time. For measuring the pupil's constriction velocity, the test is done under a low light with controlled intensity and duration. The inventors compare this data of an AD patient with some predefined standard data taken from normal persons. Other researchers have obtained mixed results, with some reporting that the method works and others that it does not.

8. Zhou et al, in U.S. Pat. No. 6,988,995 are using a diode laser with 780 nm radiation. The laser light is first collimated and then scans in 2 dimensions by a resonance scanner and a galvanometer scanner. The scanned beam is taking data from the eye RNFL (retinal nerve fiber layers) compared with some standard signatures. The inventors claim that their method is using birefringence data of the structural elements of the eye with sufficient accuracy which is required to identify the effects of AD in the RNFL. The drawback of the invention is that there is no experimental data to support the invention. In this patent the laser power is not known and its safety is questionable. Even the inventors are not sure that the method is practical and there is no proof that the RNFL affected by AD.

The present arts have at least three major drawbacks. The first one is high intensity laser scanning which is harmful to the patient's eyes. The second problem of some of the existing disclosed methods is the requirement of large apparatus which makes testing inconvenient to be done in Doctors' office. The third drawback is the lack of a very sensitive and highly efficient testing method which is required for early detection of the AD symptoms.

From the above discussions of the prior arts, the only presently known means of positively proving and demonstration of AD case in a person can only be achieved by a brain biopsy or a postmortem examination to determine existing of the plaque (amyloid) in brain tissue. It is overwhelmingly obvious that there has been remained a large demand for an accurate diagnosis for AD symptoms which do not include brain biopsy, surgery, or even using the harmful high dose MRI and CT.

In view of the foregoing, there is a definite need for a simple non-invasive system that a) can detect early sign of Alzheimer's b) is low cost, c) is safe and simple to operate, and portable, and d) has high sensitivity and specificity. Systems to address the same are provided in further detail herein.

BRIEF SUMMARY

A primary objective of the methods and apparatuses of the present disclosure is to provide a new non-invasive system for hemorrhage detection and imaging in trauma injury situation in hospitals, in the battlefield, and/or in other emergency situations/locations, using an all fiber portable terahertz imaging system. Exemplary terahertz images generated from said systems contain detailed spectral information which can be analyzed for spectral signature characteristic of the hemorrhage and its severity.

Terahertz waves are a segment of electromagnetic waves. Terahertz waves are bounded between millimeter waves (less than $1 \times 10^{11}$ Hz) and photonics waves (greater than $1 \times 10^{13}$). The electromagnetic frequencies lower than terahertz band cover mm waves (microwaves), while the electromagnetic frequencies higher than terahertz band cover near infrared through visible spectrum. Terahertz waves can be used for time domain and frequency domain imaging. Terahertz waves are highly sensitive to bio-molecules and water, and they have been applied to many biomedical applications including diagnosing various types of cancer.

Terahertz radiation is completely unionized with photon energies more than six orders of magnitude less than soft x-rays. Most terahertz medical applications require on the order of few milliwatts (mws) of power which makes terahertz radiation completely safe for use by humans or on human subjects.

When using optical fibers in combination with ultrashort pulses, the linear chromatic dispersion and nonlinear effects in the fiber have to be considered. Both effects lead to pulse broadening, which makes a terahertz time domain spectroscopy measurement not feasible without a proper compensation setup. The issue has been solved by using two optical diffraction gratings. This can also be accomplished by incorporating a pre-compression via a certain length of fiber inside of the laser unit.

Existing water in living tissue limits the penetration depth of terahertz energy to few millimeters, which is just sufficient for the detection of hemorrhage. The present methods and apparatuses disclosure herein do not require the introduction of harmful agents into the tissue.

Spectroscopic measurements can be performed by placing an imaging patch probe (flat end) on the patient's skin. The measurement can be accomplished using pulsed terahertz time-domain imaging technique providing a three dimensional (tomography) image of the skin.

The terahertz imaging patch probe can comprise a miniaturized fiber-coupled terahertz system. The patch probe can consist of a terahertz radiation transmitter and detector modules where the transmitter sends the signal to the skin and the detector receives the signal from the skin. Both the transmitter and detector modules can be driven by a femtosecond laser that can operate either at or above 1.5 micron or 800 nm, for example. The transmitter and detector modules can be combined into one module which is called a transceiver. The patch probe can also consist of optical lenses to focus the terahertz beam on to the skin. The cross section of the patch probe can be at or about 2.5×25 cm to ensure a high signal to noise ratio. The end surface of the patch probe will be made of material which could be highly transparent to terahertz radiation (i.e. polyethylene).

The patch probe can have two degrees of freedom on the skin surface. The present apparatus gathers data in three spatial dimensions, as referenced in further detail herein. Initially, a region is selected on the skin and a line image is constructed through the depth of the skin. The depth of the skin is binned according to the desired spatial resolution and signal-to-noise ratio. Then, the patch probe can be moved in one direction on the skin surface to create successive line images along the depth of the skin. Finally, the patch probe can be used/scanned in other direction on the skin surface. The information can be gathered over the entire area of interest, as desired. A tomography can then be constructed from some or all of the gathered data. The scanning can be performed by a commercially available galvanometer scanner.

A better understanding can be achieved with reference to the detailed description of the disclosed method and apparatus and with reference to the drawings. The description represents a particular case to realize the disclosed method and apparatus and is not intended to define the sole scope of invention.

Exemplary non-invasive systems of the present disclosure a) can detect an early sign of hemorrhage as well as the degree of severity, b) are low cost, c) are safe and simple to operate, and portable, and d) have high sensitivity and specificity.

In an exemplary embodiment of an apparatus for non-invasive hemorrhage detection and imaging in trauma injury using all fiber coupled portable terahertz imaging system of the present disclosure, the apparatus/system comprises one or more of the following: a) an electromagnetic source (also referred to herein as a laser or a femtosecond pulse laser); and/or b) a dispersion compensation unit (also referred to herein as an optical diffraction grating or gratings); and/or c) a rapid scanning optical delay line (RSOD); and/or d) a transmitter module having a transmitter chip; and/or e) a detector module having a detector chip; and/or f) one or more optical lenses; and/or g) a scanning system to scan the skin in two dimensions (also referred to as a galvanometer scanner); and/or h) a handheld patch probe (HPP); and/or i) a matching amplifier coupled to the detector; and/or j) a display unit to receive data from the matching amplifier to interpret the test results.

In an exemplary embodiment of an apparatus/system of the present disclosure, the electromagnetic source is a femtosecond pulsed laser with wavelength of about 1.5 µm.

In an exemplary embodiment of an apparatus/system of the present disclosure, the dispersion compensation unit can be either an optical diffraction gratings unit, or a pre-compression unit via a certain length of fiber inside of the laser unit.

In an exemplary embodiment of an apparatus/system of the present disclosure, the rapid scanning optical delay line could be either micro-opto-electro-mechanical system or a rotating planar reflector system.

In an exemplary embodiment of an apparatus/system of the present disclosure, the transmitter and detector modules and optical lenses are inside of the handheld patch probe.

In an exemplary embodiment of an apparatus/system of the present disclosure, the display unit is mounted on the handheld patch probe.

In an exemplary embodiment of an apparatus/system of the present disclosure, the scanning of the probe on the skin surface will be performed by a commercially available galvanometer scanner.

In an exemplary embodiment of a method for non-invasive hemorrhage detection and imaging in the trauma injury situation using all fiber coupled portable terahertz imaging system of the present disclosure, the method comprises the steps of a) generating and tailoring a terahertz signal; b) splitting the terahertz signal to scanning and reference signals; c) illuminating the skin with a focused scanning terahertz beam; d) redirecting the reflection from the skin into detector; e) inserting the output of the terahertz detector to a matching amplifier; and f) inserting the output of the matching amplifier to a display unit.

In an exemplary embodiment of a method of the present disclosure, the terahertz signal generator covers terahertz bandwidth from 200-10000 GHz.

In an exemplary embodiment of a method of the present disclosure, the method further comprises the step of setting up a terahertz detector to detect the difference in signals from the reflected terahertz signal from the skin and the reference signal split from the terahertz signal generator.

In an exemplary embodiment of a method of the present disclosure, the method further comprises the step of using matching amplifier to improve the detected signal.

In an exemplary embodiment of a method of the present disclosure, the method further comprises the step of forming an image from the reflected pulses at each layer perpendicular to the skin surface.

In an exemplary embodiment of a method of the present disclosure, the method further comprises the steps of comparing the images with a calibrated reference stored in memory; combining the images at different layers to obtain the tomography of the skin; indicating regions of coincidence and regions of non-coincidence; and showing the result in display unit.

In an exemplary embodiment of a method of the present disclosure, the method further comprises the step of providing a three dimensional image of the skin in real time which includes spectral signature characteristic of the hemorrhage and its severity.

In an exemplary embodiment of a method of the present disclosure, the image is comprised of a plurality of horizontal bands, each band being adjacent to another, with equal bandwidths In an exemplary embodiment of a method of the present disclosure, the method further comprises the steps of comparing the images with a calibrated reference stored in memory, indicating regions of coincidence and regions of non-coincidence, and combining the images at different layers to obtain the tomography of the skin to characterize the degree of hemorrhage.

The present disclosure includes disclosure of a control module, as shown and described herein.

The present disclosure includes disclosure of a handheld patch probe, as shown and described herein.

The present disclosure includes disclosure of a system, comprising a control module of the present disclosure and a handheld patch probe of the present disclosure, wherein the handheld patch probe is coupled to the control module and/or configured to communicate with the control module.

The present disclosure includes disclosure of methods to use a control module and a handheld patch probe, to obtain skin information/data useful to determine a severity of a hemorrhage.

A primary objective of the methods and apparatuses of the present disclosure is to provide a new non-invasive system for early detection of Alzheimer's through eye cornea or aqueous humor, using an all fiber portable terahertz imaging system. Exemplary terahertz images generated from said systems contain detailed spectral information which can be analyzed for spectral signature characteristic of the Alzheimer's and its severity.

Terahertz waves are a segment of electromagnetic waves. Terahertz waves are bounded between millimeter waves (less than $1 \times 10^{11}$ Hz) and photonics waves (greater than $1 \times 10^{13}$). The electromagnetic frequencies lower than terahertz band cover mm waves (microwaves), while the electromagnetic frequencies higher than terahertz band cover near infrared through visible spectrum (7). Terahertz waves can be used for time domain and frequency domain imaging. Terahertz waves are highly sensitive to bio-molecules and water, and they have been applied to many biomedical applications including diagnosing various types of cancer.

Terahertz radiation is completely unionized with photon energies more than six orders of magnitude less than soft x-rays. Most terahertz medical applications require on the order of few milliwatts (mws) of power which makes terahertz radiation completely safe for use by humans or on human subjects.

When using optical fibers in combination with ultrashort pulses, the linear chromatic dispersion and nonlinear effects in the fiber have to be considered. Both effects lead to pulse broadening, which makes a terahertz time domain spectroscopy measurement not feasible without a proper compensation setup. The issue has been solved by using two optical diffraction gratings. This can also be accomplished by incorporating a pre-compression via a certain length of fiber inside the laser unit.

Existing water in living tissue limits the penetration depth of terahertz energy to few millimeters, which is just sufficient for the detection of Beta Amyloid. The present methods and apparatuses disclosure herein do not require the introduction of harmful agents into the tissue.

Spectroscopic measurements can be performed by placing an imaging patch probe in front of the patient's eye. The measurement can be accomplished using pulsed terahertz time-domain imaging technique providing a three dimensional (tomography) image of the eye cornea.

The eye cornea may move with respect to the imaging patch probe during the test if the patient cannot hold their head stationary. Calculations have indicated that the imaging speed is around one millisecond for one measurement compared to the time of a patient pulse/motion which is around 15 milliseconds. This is faster than the head motion and hence the head is stationary for all practical purposes as viewed by the terahertz radiation.

The terahertz imaging patch probe can comprise a miniaturized fiber-coupled terahertz system. The patch probe can consist of a terahertz radiation transmitter and detector modules where the transmitter sends the signal to the cornea and the detector receives the signal from the cornea. Both the transmitter and detector modules can be driven by a femtosecond laser that can operate either at 1.5 micron or 800 nm, for example. The transmitter and detector modules can be combined into one module which is called a transceiver. The patch probe can also consist of optical lenses to focus the terahertz beam on to the cornea. The cross section of the patch probe can be at or about 2.5×25 cm to ensure a high signal to noise ratio. The end surface of the patch probe will be made of material which could be highly transparent to terahertz radiation (i.e. polyethylene).

The patch probe can have degrees of freedom. The present apparatus gathers data in three spatial dimensions, as referenced in further detail herein. Initially, a region is selected on the cornea and a line image is constructed through the depth of the cornea. The depth of the cornea is binned according to the desired spatial resolution and signal-to-noise ratio. Then, the patch probe can be moved in one direction to create successive line images along the depth of the cornea. Finally, the patch probe can be used/scanned in other direction. The information can be gathered over the entire area of interest, as desired. A tomography can then be constructed from some or all of the gathered data. The scanning can be performed by a commercially available galvanometer scanner.

A better understanding can be achieved with reference to the detailed description of the disclosed method and apparatus and with reference to the drawings. The description represents a particular case to realize the disclosed method and apparatus and is not intended to define the sole scope of invention.

Exemplary non-invasive systems of the present disclosure a) can detect an early sign of Alzheimer's b) are low cost, c) are safe and simple to operate, and portable, and d) have high sensitivity and specificity.

In an exemplary embodiment of an apparatus for non-invasive early detection of Alzheimer's using all fiber coupled portable terahertz imaging system of the present disclosure, the apparatus/system comprises one or more of the following: a) an electromagnetic source (also referred to herein as a laser or a femtosecond pulse laser); and/or b) a dispersion compensation unit (also referred to herein as an optical diffraction grating or gratings); and/or c) a rapid scanning optical delay line (RSOD); and/or d) a transmitter module having a transmitter chip; and/or e) a detector module having a detector chip; and/or f) one or more optical lenses; and/or g) a scanning system to scan the cornea in two dimensions (also referred to as a galvanometer scanner); and/or h) a handheld patch probe (HPP); and/or i) a matching amplifier coupled to the detector; and/or j) a display unit to receive data from the matching amplifier to interpret the test results.

In an exemplary embodiment of an apparatus/system of the present disclosure, the electromagnetic source is a femtosecond pulsed laser with wavelength of 1.5 µm.

In an exemplary embodiment of an apparatus/system of the present disclosure, the dispersion compensation unit can be either an optical diffraction gratings unit, or a pre-compression unit via a certain length of fiber inside of the laser unit.

In an exemplary embodiment of an apparatus/system of the present disclosure, the rapid scanning optical delay line could be either micro-opto-electro-mechanical system or a rotating planar reflector system.

In an exemplary embodiment of an apparatus/system of the present disclosure, the transmitter and detector modules and optical lenses are inside of the handheld patch probe.

In an exemplary embodiment of an apparatus/system of the present disclosure, the display unit is mounted on the handheld patch probe.

In an exemplary embodiment of an apparatus/system of the present disclosure, the scanning of the probe will be performed by a commercially available galvanometer scanner.

In an exemplary embodiment of a method for non-invasive early detection of Alzheimer's using all fiber coupled portable terahertz imaging system of the present disclosure, the method comprises the steps of a) generating and tailoring a terahertz signal; b) splitting the terahertz signal to scanning and reference signals; c) illuminating the cornea with a focused scanning terahertz beam; d) redirecting the reflection from the cornea into detector; e) inserting the output of the terahertz detector to a matching amplifier; and f) inserting the output of the matching amplifier to a display unit.

In an exemplary embodiment of a method of the present disclosure, the terahertz signal generator covers terahertz bandwidth from 200-10000 GHz.

In an exemplary embodiment of a method of the present disclosure, the method further comprises the step of setting up a terahertz detector to detect the difference in signals from the reflected terahertz signal from the cornea and the reference signal split from the terahertz signal generator.

In an exemplary embodiment of a method of the present disclosure, the method further comprises the step of using matching amplifier to improve the detected signal.

In an exemplary embodiment of a method of the present disclosure, the method further comprises the step of forming an image from the reflected pulses at each layer perpendicular to the cornea surface.

In an exemplary embodiment of a method of the present disclosure, the method further comprises the steps of comparing the images with a calibrated reference stored in memory; combining the images at different layers to obtain the tomography of the cornea; indicating regions of coincidence and regions of non-coincidence; and showing the result in display unit.

In an exemplary embodiment of a method of the present disclosure, the method further comprises the step of providing a three dimensional image of the cornea in real time which includes spectral signature characteristic of the Beta Amyloid in the cornea/AH In an exemplary embodiment of a method of the present disclosure, the image is comprised of a plurality of horizontal bands, each band being adjacent to another, with equal bandwidths In an exemplary embodiment of a method of the present disclosure, the method further comprises the steps of comparing the images with a calibrated reference stored in memory, indicating regions of coincidence and regions of non-coincidence, and combining the images at different layers to obtain the tomography of the cornea for the early detection of Alzheimer's.

The present disclosure includes disclosure of a control module, as shown and described herein.

The present disclosure includes disclosure of a handheld patch probe, as shown and described herein.

The present disclosure includes disclosure of a system, comprising a control module of the present disclosure and a handheld patch probe of the present disclosure, wherein the handheld patch probe is coupled to the control module and/or configured to communicate with the control module.

The present disclosure includes disclosure of methods to use a control module and a handheld patch probe, to obtain cornea information/data useful to determine the existence of the Beta Amyloid.

The present disclosure includes disclosure of an imaging system, comprising a control module, comprising a femtosecond pulsed laser configured to generate an output light beam; a dispersion compensation unit configured to receive the output light beam and transmit a laser light beam generated based upon the output light beam; a beam splitter configured to receive the laser light beam and divide the laser light beam into a pump light beam and a reference light beam; and a rapid scanning optical delay line configured to receive the pump light beam and transmit an exit light beam generated based upon the pump light beam; and a patch probe, comprising a transmitter module configured to receive the exit light beam from the control module and to transmit terahertz waves generated based upon the exit light beam; an optics lens configured to direct the terahertz waves toward a portion of a patient; and a detector module configured to a) receive a reflected terahertz signal from the patient, the reflected terahertz signal based upon the terahertz waves directed toward the patient; and b) receive the reference light from the control unit; and c) combine the reflected terahertz signal and the reference light to generate patient data.

The present disclosure includes disclosure of an imaging system, wherein the output light beam is gated by time domain pulses measurable in femtoseconds.

The present disclosure includes disclosure of an imaging system, wherein the patch probe further comprises a galvanometer scanner, configured to scan the terahertz waves in two directions.

The present disclosure includes disclosure of an imaging system, wherein the portion of the patient comprises skin of the patient, and wherein the patient data indicates a hemorrhage within the patient.

The present disclosure includes disclosure of an imaging system, wherein the control module or the patch probe further comprises a display unit configured to display the patient data or an image generated based upon the patient data.

The present disclosure includes disclosure of an imaging system, wherein the patch probe is configured as a hand-held patch probe.

The present disclosure includes disclosure of an imaging system, configured to generate a skin image based upon the patient data.

The present disclosure includes disclosure of an imaging system, further comprising a data acquisition and processing system, comprising a processor in operative communication with a storage medium, wherein the processor is operable to process the patient data to generate a skin image using software stored upon the storage medium, wherein the storage medium is configured to store at least one of the patient data and/or the skin image.

The present disclosure includes disclosure of an imaging system, wherein the rapid scanning optical delay line comprises a micro-opto-electro-mechanical system.

The present disclosure includes disclosure of an imaging system, wherein the rapid scanning optical delay line comprises a rotating planar reflector system.

The present disclosure includes disclosure of an imaging system, wherein the dispersion compensation unit is selected from the group consisting of an optical diffraction gratings unit and a pre-compression unit comprising a certain length of fiber inside of the control module.

The present disclosure includes disclosure of an imaging system, wherein the portion of the patient comprises aqueous humor of an eye of the patient, and wherein the patient data indicates an Alzheimer's disease condition of the patient.

The present disclosure includes disclosure of an imaging system, wherein the portion of the patient comprises a cornea of an eye of the patient, and wherein the patient data indicates an Alzheimer's disease condition of the patient.

The present disclosure includes disclosure of an imaging system, configured to generate a cornea/aqueous humor image based upon the patient data.

The present disclosure includes disclosure of an imaging system, further comprising a data acquisition and processing system, comprising a processor in operative communication with a storage medium, wherein the processor is operable to process the patient data to generate a cornea/aqueous humor image using software stored upon the storage medium, wherein the storage medium is configured to store at least one of the patient data and/or the cornea/aqueous humor image.

The present disclosure includes disclosure of a method for non-invasive patient condition detection, comprising the steps of: a) generating and tailoring a terahertz signal; b) splitting the terahertz signal into a scanning signal and a reference signal; c) illuminating a surface of a patient with a focused scanning terahertz beam; d) redirecting reflection of the focused scanning terahertz beam from the surface of the patient into a detector; and e) combining the reflection of the focused scanning terahertz beam with the reference signal to generate patient data The present disclosure includes disclosure of a method for non-invasive patient condition detection, further comprising the step of forming an image from the patient data based upon reflected pulses of the reflection of the focused scanning terahertz beam at each layer perpendicular to the surface of the patient The present disclosure includes disclosure of a method for non-invasive patient condition detection, wherein the surface of the patient comprises skin of the patient, and wherein the method further comprises the step of generating a three dimensional image of the skin in real time which includes a spectral signature characteristic of a detected hemorrhage of the patient and its severity.

The present disclosure includes disclosure of a method for non-invasive patient condition detection, wherein the surface of the patient comprises a cornea of the patient, and wherein the method further comprises the step of generating a three dimensional image of the cornea/aqueous humor in real time which includes a spectral signature characteristic of Alzheimer's disease of the patient and its severity.

The present disclosure includes disclosure of an imaging system, comprising a control module, comprising a femtosecond pulsed laser configured to generate an output light beam, wherein the output light beam is gated by time domain pulses measurable in femtoseconds; a dispersion compensation unit configured to receive the output light beam and transmit a laser light beam generated based upon the output light beam; a beam splitter configured to receive the laser light beam and divide the laser light beam into a pump light beam and a reference light beam; and a rapid scanning optical delay line configured to receive the pump light beam and transmit an exit light beam generated based upon the pump light beam; and a patch probe, comprising a transmitter module configured to receive the exit light beam from the control module and to transmit terahertz waves generated based upon the exit light beam; an optics lens configured to direct the terahertz waves toward a portion of a patient; and a detector module configured to a) receive a reflected terahertz signal from the patient, the reflected terahertz signal based upon the terahertz waves directed toward the patient; and b) receive the reference light from the control unit; and c) combine the reflected terahertz signal and the reference light to generate patient data; and a display unit configured to display the patient data or an image generated based upon the patient data; and a data acquisition and processing system, comprising a processor in operative communication with a storage medium, wherein the processor is operable to process the patient data to generate the image using software stored upon the storage medium, wherein the storage medium is configured to store at least one of the patient data and/or the image.

The present disclosure includes disclosure of an imaging system, the portion of the patient comprises aqueous humor of an eye of the patient, and wherein the patient data indicates an Alzheimer's disease condition of the patient.

The present disclosure includes disclosure of an imaging system, the portion of the patient comprises a cornea of an eye of the patient, and wherein the patient data indicates an Alzheimer's disease condition of the patient.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein.

Figure 1:
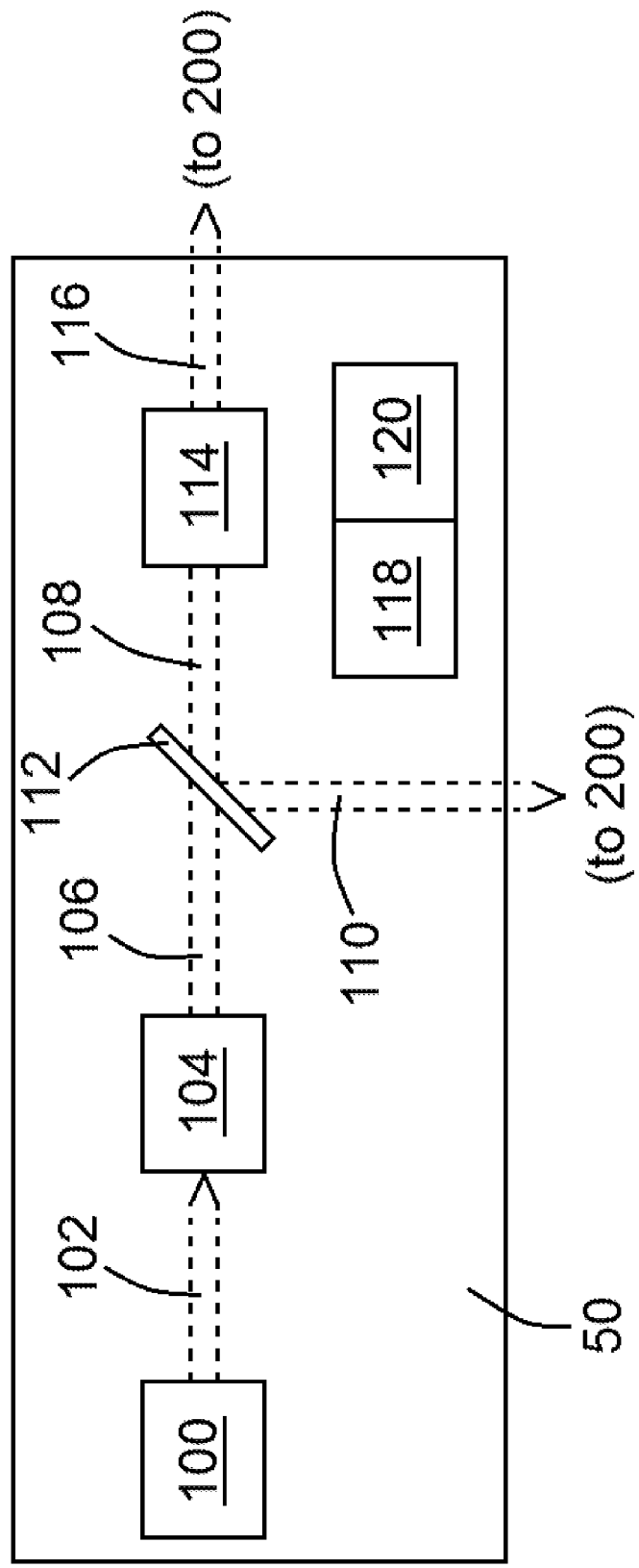
FIG. 1 shows a simplified block diagram of a control unit, according to at least one embodiment of the present disclosure.

An overview of the features, functions and/or configurations of the components depicted in the various figures will now be presented. It should be appreciated that not all of the features of the components of the figures are necessarily described. Some of these non-discussed features, such as various couplers, etc., as well as discussed features are inherent from the figures themselves. Other non-discussed features may be inherent in component geometry and/or configuration.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

An exemplary control module 50 of the present disclosure is shown in block diagram format in FIG. 1. As shown in FIG. 1, an exemplar control module 50 can comprise several elements, including a femtosecond pulsed laser 100 configured to generate an output beam 102 (also referred to as a fiber carrier laser light) having a wavelength of at or about 1.5 µm, for example.

The output beam 102 generated by the laser 100 is gated by time domain pulses, the duration of which are preferably measured in femtoseconds in various embodiments. The output beam 102 from the pulsed laser 100 connects to (and/or is otherwise directed to and/or received by) optical diffraction gratings 104, the output of which is referred to herein as the laser light 106. The laser light 106 (namely the output beam 102 that traveled through the optical diffraction gratings 104) will split into a pump light 108 and a reference light 110 by way of a beam splitter 112 in line with the laser light 106. The pump light 108 will then enter a rapid scanning optical delay line (RSOD) 114 and exit the same as exited light 116. At least two different configurations for RSOD are included within the present disclosure. In a first configuration, a micro-opto-electro-mechanical system (MOEMS) is used, such as referenced within a U.S. Pat. No. 6,839,172, entitled "Enhanced sampling rate in time domain imaging using MOEMS scanning optical delay line." In a second configuration, a rotating planar reflector (RPR) is used with a delay line repetition rate of more than 800 Hz.

Use for Non-Invasive Hemorrhage Detection

Figure 2A:
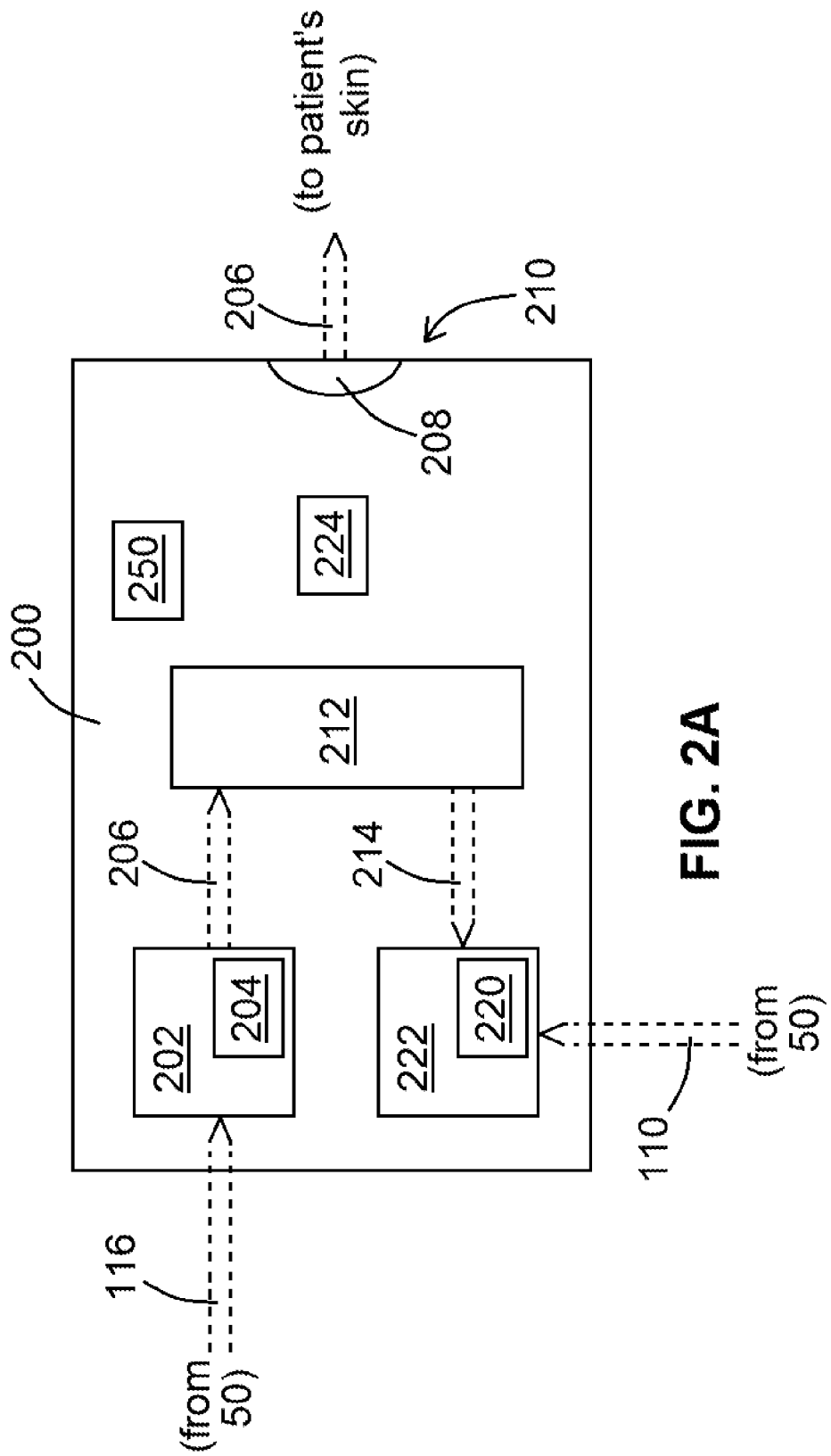
FIG. 2A and FIG. 2B show simplified block diagrams of diagnostic patch probes, according to embodiments of the present disclosure.

The exited light 116 (namely the pump light 108 after passing through RSOD 114), can enter a transmitter module 202, such as shown in FIG. 2A, which is inside of, and comprises part of, a handheld patch probe (HPP) 200. A transmitter chip 204 inside of the transmitter module 202 can comprise a photoconductive antenna (PCA) fabricated on a semi-insulating InGaAs wafer, for example. The transmitter module 202, in at least one embodiment, requires a direct current (DC) voltage for biasing. All components required for HPP 200 operation can exist outside of the HPP 200, such as within a control unit 50, referenced in further detail herein.

The terahertz waves 206 emitted from the transmitter chip 204 of the transmitter module 202 are focused by an optics lens 208 to the patient's skin (when HPP 200 is positioned thereupon) through the end 210 of the patch probe 200, which is made of material with high transparency to terahertz radiation. A galvanometer scanner 212 is positioned between the transmitter module 202 and the end 210 of the patch probe 200 to scan the beam (the terahertz waves 206) on the skin surface in two directions.

The reflection of the terahertz waves 206 from the patient's skin (reflected as a reflected terahertz signal 214) will be detected by a detector chip 220 inside of the detector module 222 which is inside of the hand-held patch probe 200. The detector chip 220, in at least one embodiment, has the same structure and principles as discussed for the transmitter chip 204. All of the electrical and optical parts can be affixed within the HPP 200 using epoxy or another adhesive or connector, for example.

The reference light 110 (generated using control unit 50, as shown in FIG. 1) enters the detector module 222 at the exact/same time arrival as the reflected terahertz signal 214 carrying information regarding the patient's skin. The mixing of these two terahertz waves (the reference light 110 and the reflected terahertz signal 214) within the detector module 222 will detect the skin information/data, which is comprised of a spectral signature characteristic of the hemorrhage and its severity.

The skin information/data from the detector chip 220 of the detector module 222 can be transferred to the matching amplifier 118 and data acquisition system 120 (as shown in FIG. 1) and then transferred to the display unit 224 mounted on the HPP 200. Alternatively, the diagnosis results (the skin information/data) could be transmitted locally and/or to a medical center or other third party by means such as wireless and/or wired communications, such as using transmitter module 202, detector module 222, and/or a data transmitter 250, such as shown in FIG. 2A, configured to wirelessly transmit data and/or transmit data via wired communication to control unit 50, data acquisition and processing system 120, or another system or device, as may be desired, which is then configured to receive the transmitted data. Using the high speed scanning delay line allows the multiple layers of information of the skin to be collected. In addition, a representative tomography of the skin can be constructed and displayed on display unit 224 or otherwise.

In various embodiments, an exemplary skin image 300 of the present disclosure, generated using the obtained skin information/data) is comprised of a plurality of horizontal bands 302, each band 302 being adjacent to another, with equal bandwidths and comprised of a plurality of pixels 304 where each pixel 304 being adjacent to another in the horizontal direction. The images 300 with a calibrated reference are stored in a memory, indicating regions of coincidence and region of non-coincidence, and combining the images 300 at vertical direction to obtain the three dimensional images of the skin.

Figure 4:
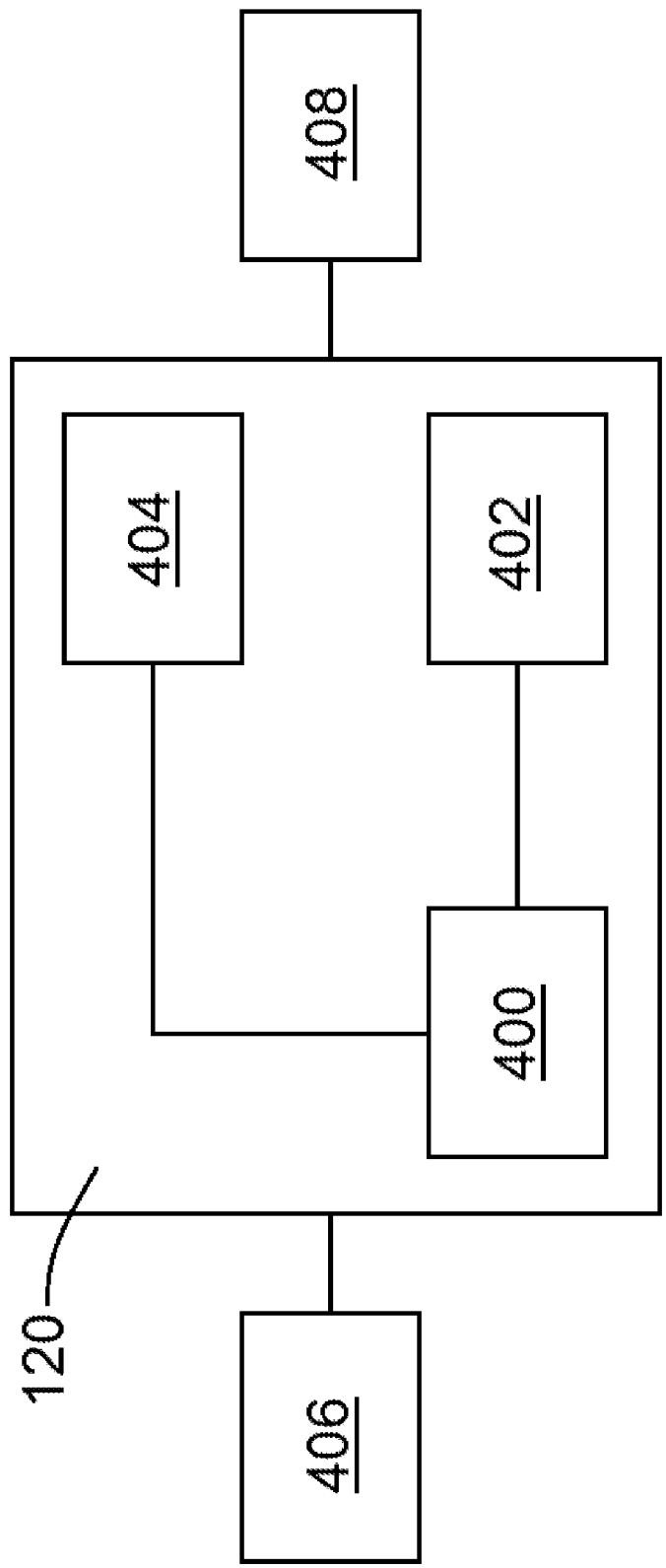
FIG. 4 shows elements of a data processing system in block diagram format, according to at least one embodiment of the present disclosure.

Skin/information data, as well as skin images 300 generated using said data, can be processed using an exemplary data acquisition system 120 shown in FIG. 4. As shown therein, an exemplary data acquisition system 120 of the present disclosure can comprise a processor 400 in operative communication with a storage medium 402 (such as a hard drive, an optical disc drive, a solid state drive, and the like), whereby system memory 404 facilitates the operation of the processor 400 and the storage medium 402 as needed. Various input devices 406, such as keyboards, touchpads, mice, etc., and/or various output devices 408, such as displays/monitors, speakers, printers, data transmitters, and the like, can be coupled to, or form part of, the data acquisition systems 120 of the present disclosure. Skin/information data can be received by the data acquisition system 120 and processed using the processor 400 and processing software stored on the storage medium 402, along with the operation of one or more input devices 406 as desired, so to generate skin images 300, which can also be stored on the storage medium 402 and displayed, depicted, or otherwise transmitted using one or more output devices 408.

Use for Non-Invasive Early Detection of Alzheimer's Disease

Figure 2B:
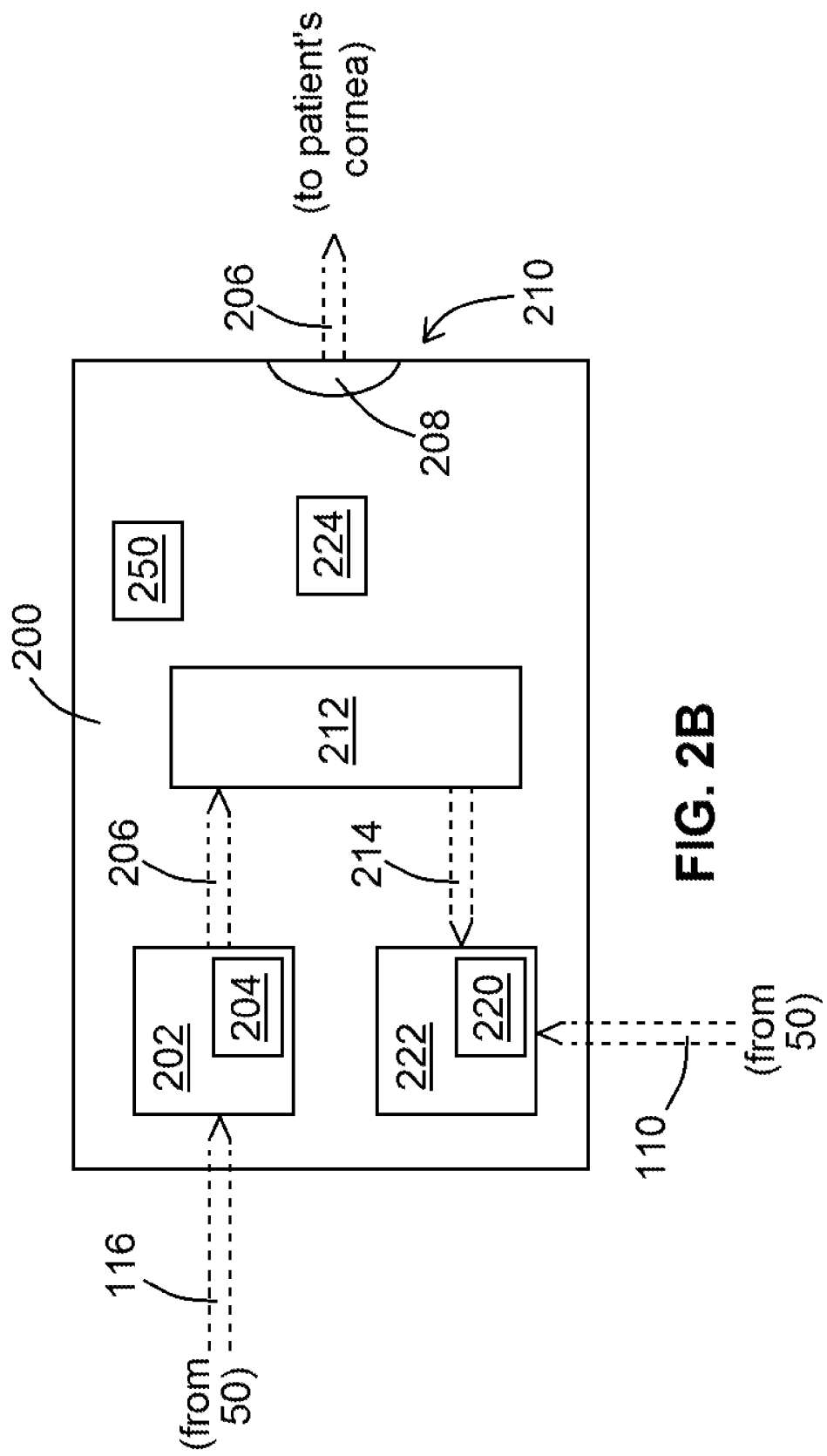
Figure 3:
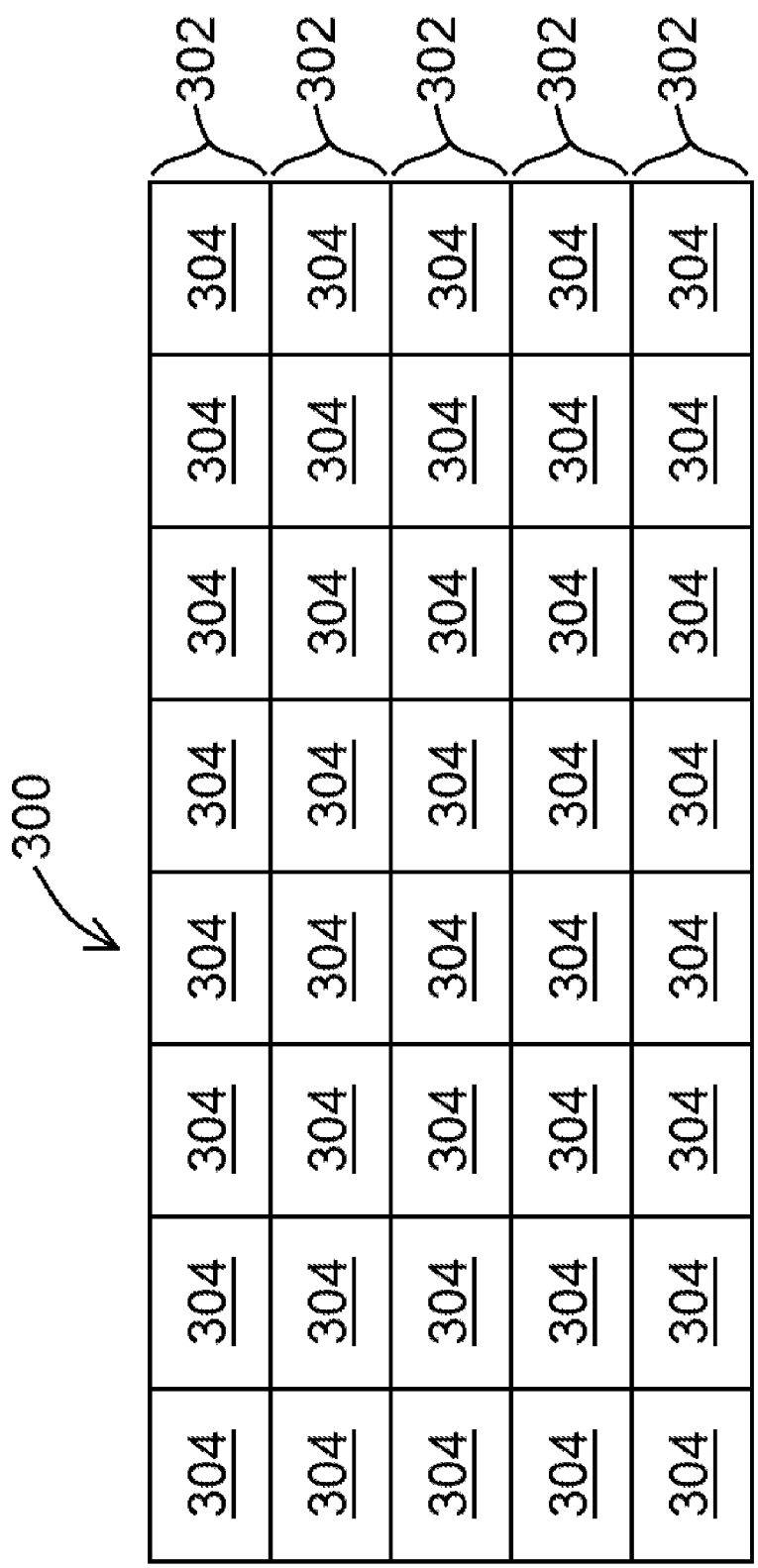
FIG. 3 shows an image, according to at least one embodiment of the present disclosure.

The exited light 116 (namely the pump light 108 after passing through RSOD 114), can enter a transmitter module 202, such as shown in FIG. 2B, which is inside of, and comprises part of, a handheld patch probe (HPP) 200. A transmitter chip 204 inside of the transmitter module 202 can comprise a photoconductive antenna (PCA) fabricated on a semi-insulating InGaAs wafer, for example. The transmitter module 202, in at least one embodiment, requires a direct current (DC) voltage for biasing. All components required for HPP 200 operation can exist outside of the HPP 200, such as within a control unit 50, referenced in further detail herein.

The terahertz waves 206 emitted from the transmitter chip 204 of the transmitter module 202 are focused by an optics lens 208 to the patient's cornea (when HPP 200 is positioned thereupon) through the end 210 of the patch probe 200, which is made of material with high transparency to terahertz radiation. A galvanometer scanner 212 is positioned between the transmitter module 202 and the end 210 of the patch probe 200 to scan the beam (the terahertz waves 206) on the cornea surface in two directions.

The reflection of the terahertz waves 206 from the patient's aqueous humor (reflected as a reflected terahertz signal 214) will be detected by a detector chip 220 inside of the detector module 222 which is inside of the hand-held patch probe 200. The detector chip 220, in at least one embodiment, has the same structure and principles as discussed for the transmitter chip 204. All of the electrical and optical parts can be affixed within the HPP 200 using epoxy or another adhesive or connector, for example.

The reference light 110 (generated using control unit 50, as shown in FIG. 1) enters the detector module 222 at the exact/same time arrival as the reflected terahertz signal 214 carrying information regarding the patient's cornea. The mixing of these two terahertz waves (the reference light 110 and the reflected terahertz signal 214) within the detector module 222 will detect the cornea information/data, which is comprised of a spectral signature characteristic of the AD and its severity.

The cornea information/data from the detector chip 220 of the detector module 222 can be transferred to the matching amplifier 118 and data acquisition system 120 (as shown in FIG. 1) and then transferred to the display unit 224 mounted on the HPP 200. Alternatively, the diagnosis results (the cornea/aqueous humor information/data) could be transmitted locally and/or to a medical center or other third party by means such as wireless and/or wired communications, such as using transmitter module 202, detector module 222, and/or a data transmitter 250, such as shown in FIG. 2A, configured to wirelessly transmit data and/or transmit data via wired communication to control unit 50, data acquisition and processing system 120, or another system or device, as may be desired, which is then configured to receive the transmitted data. Using the high speed scanning delay line allows the multiple layers of information of the cornea to be collected. In addition, a representative tomography of the cornea can be constructed and displayed on display unit 224 or otherwise.

In various embodiments, an exemplary cornea image 300 of the present disclosure, generated using the obtained cornea information/data) is comprised of a plurality of horizontal bands 302, each band 302 being adjacent to another, with equal bandwidths and comprised of a plurality of pixels 304 where each pixel 304 being adjacent to another in the horizontal direction. The images 300 with a calibrated reference are stored in a memory, indicating regions of coincidence and region of non-coincidence, and combining the images 300 at vertical direction to obtain the three dimensional images of the cornea.

Cornea/information data, as well as cornea images 300 generated using said data, can be processed using an exemplary data acquisition system 120 shown in FIG. 4. As shown therein, an exemplary data acquisition system 120 of the present disclosure can comprise a processor 400 in operative communication with a storage medium 402 (such as a hard drive, an optical disc drive, a solid state drive, and the like), whereby system memory 404 facilitates the operation of the processor 400 and the storage medium 402 as needed. Various input devices 406, such as keyboards, touchpads, mice, etc., and/or various output devices 408, such as displays/monitors, speakers, printers, data transmitters, and the like, can be coupled to, or form part of, the data acquisition systems 120 of the present disclosure. Cornea/information data can be received by the data acquisition system 120 and processed using the processor 400 and processing software stored on the storage medium 402, along with the operation of one or more input devices 406 as desired, so to generate cornea images 300, which can also be stored on the storage medium 402 and displayed, depicted, or otherwise transmitted using one or more output devices 408.

While various embodiments of systems and devices for non-invasive internal hemorrhage detection and for non-invasive early detection of Alzheimer's Disease using an all fiber portable terahertz imaging system and methods of using the same have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. An imaging system, comprising:
   a control module, comprising:
   a femtosecond pulsed laser generator within the control module and configured to generate an output light beam;
   a dispersion compensation unit configured to receive the output light beam and transmit a laser light beam generated based upon the output light beam, wherein the dispersion compensation unit comprises two optical diffraction gratings;
   a beam splitter configured to receive the laser light beam and divide the laser light beam into a pump light beam and a reference light beam;
   wherein the output light beam connects to the dispersion compensation unit before connecting to the beam splitter;
   a rapid scanning optical delay line configured to receive the pump light beam and transmit an exit light beam generated based upon the pump light beam; and wherein the control module is outside of a non-invasive handheld patch probe;
the patch probe, comprising:
a transmitter module configured to receive the exit light beam from the control module and to transmit terahertz waves generated based upon the exit light beam;
an optics lens configured to direct the terahertz waves toward a skin of a patient; and
a detector module configured to:
a) receive a reflected terahertz signal from the skin of the patient, the reflected terahertz signal based upon the terahertz waves directed toward the patient and indicative of a hemorrhage below the patient's skin;
b) receive the reference light from the control unit; and
c) combine the reflected terahertz signal and the reference light to generate patient data; and
wherein the imaging system is portable.

2. The imaging system of claim 1, wherein the output light beam is gated by time domain pulses measurable in femtoseconds.

3. The imaging system of claim 1, wherein the patch probe further comprises a galvanometer scanner, configured to scan the terahertz waves in two directions.

4. The imaging system of claim 1, wherein the patient data indicates a hemorrhage under the skin of the patient.

5. The imaging system of claim 1, wherein the patch probe further comprises a display unit configured to display the patient data or an image generated based upon the patient data.

6. The imaging system of claim 1, wherein the rapid scanning optical delay line comprises a system selected from the group consisting of a micro-opto-electro-mechanical system and a rotating planar reflector system.

7. The imaging system of claim 1, configured to generate a skin image based upon the patient data.

8. The imaging system of claim 1, further comprising:
a data acquisition and processing system, comprising a processor in operative communication with a storage medium, wherein the processor is operable to process the patient data to generate a skin image using software stored upon the storage medium, wherein the storage medium is configured to store at least one of the patient data and/or the skin image.

9. A method for non-invasive patient condition detection, comprising the steps of:
a) generating and tailoring a terahertz signal
b) receiving the terahertz signal in a dispersion compensation unit;
c) compensating for pulse broadening of the terahertz signal using two optical diffraction gratings;
d) splitting the terahertz signal into a scanning signal and a reference signal after the terahertz signal has been received in the dispersion compensation unit;
e) illuminating a skin surface of a patient with a focused scanning terahertz beam;
f) redirecting reflection of the focused scanning terahertz beam from the skin of the patient into a detector;
g) combining the reflection of the focused scanning terahertz beam with the reference signal to generate patient data indicative of a hemorrhage below a patient's skin; and
h) wherein steps a) d) are performed using a control module and steps e)-g) are performed using a non-invasive handheld patch probe, and the control module comprises a laser generator within the control module and is outside the patch probe, wherein the patch probe and control module are part of a portable imaging system.

10. The method of claim 9, further comprising the step of forming an image from the patient data based upon reflected pulses of the reflection of the focused scanning terahertz beam at each layer perpendicular to the surface of the patient.

11. The method of claim 9, wherein the method further comprises the step of generating a three dimensional image of the skin in real time which includes a spectral signature characteristic of a detected hemorrhage under the skin of the patient and its severity.

12. An imaging system, comprising:
a control module, comprising:
a femtosecond pulsed laser generator within the control module and configured to generate an output light beam, wherein the output light beam is gated by time domain pulses measurable in femtoseconds;
a dispersion compensation unit configured to receive the output light beam and transmit a laser light beam generated based upon the output light beam, wherein the dispersion compensation unit comprises two optical diffraction gratings;
a beam splitter configured to receive the laser light beam and divide the laser light beam into a pump light beam and a reference light beam;
wherein the output light beam connects to the dispersion compensation unit before connecting to the beam splitter;
a rapid scanning optical delay line configured to receive the pump light beam and transmit an exit light beam generated based upon the pump light beam; and
wherein the control module is outside of a non-invasive handheld patch probe;
the patch probe, comprising:
a transmitter module configured to receive the exit light beam from the control module and to transmit terahertz waves generated based upon the exit light beam;
an optics lens configured to direct the terahertz waves toward a skin of a patient; and
a detector module configured to:
a) receive a reflected terahertz signal from the skin of the patient, the reflected terahertz signal based upon the terahertz waves directed toward the patient and indicative of a hemorrhage below the patient's skin; and
b) receive the reference light from the control unit; and
c) combine the reflected terahertz signal and the reference light to generate patient data;
a display unit configured to display the patient data or an image generated based upon the patient data;
a data acquisition and processing system, comprising a processor in operative communication with a storage medium, wherein the processor is operable to process the patient data to generate the image using software stored upon the storage medium, wherein the storage medium is configured to store at least one of the patient data and/or the image; and
wherein the imaging system is portable.

* * * * *